(12) United States Patent
Berry et al.

(10) Patent No.: US 8,726,453 B2
(45) Date of Patent: May 20, 2014

(54) MEDICAL SUCTION CLEARING APPARATUS

(75) Inventors: Mark Berry, Rancho Santa Margarita, CA (US); Kenneth D. Lewis, Rancho Santa Margarita, CA (US)

(73) Assignee: Ontium, LLC, Sandy, UT (US)

( * ) Notice: Subject to any disclaimer, the term of this patent is extended or adjusted under 35 U.S.C. 154(b) by 163 days.

(21) Appl. No.: 13/323,384

(22) Filed: Dec. 12, 2011

(65) Prior Publication Data

US 2012/0144608 A1    Jun. 14, 2012

Related U.S. Application Data

(60) Provisional application No. 61/423,015, filed on Dec. 14, 2010.

(51) Int. Cl.
*A47L 5/00* (2006.01)
*B08B 9/035* (2006.01)

(52) U.S. Cl.
USPC ...................................... 15/300.1; 15/104.05

(58) Field of Classification Search
USPC ............ 15/300.1, 345, 351, 411; 604/164.01, 604/516; 606/159
See application file for complete search history.

(56) References Cited

U.S. PATENT DOCUMENTS

| | | | | |
|---|---|---|---|---|
| 3,757,375 | A | * | 9/1973 | Strom ........................ 15/104.33 |
| 3,956,011 | A | * | 5/1976 | Carleton ........................ 134/21 |
| 2004/0199192 | A1 | | 10/2004 | Akahoshi |
| 2006/0167416 | A1 | * | 7/2006 | Mathis et al. ............ 604/164.01 |
| 2007/0179513 | A1 | * | 8/2007 | Deutsch ........................ 606/159 |
| 2009/0062772 | A1 | * | 3/2009 | Wakeford et al. ............. 604/516 |
| 2010/0229746 | A1 | | 9/2010 | Luedemann et al. |

FOREIGN PATENT DOCUMENTS

JP    2005040730    2/2005

* cited by examiner

*Primary Examiner* — Robert Scruggs
(74) *Attorney, Agent, or Firm* — K. David Crockett, Esq.; Paul J. Backofen, Esq.; Crockett & Crockett, PC

(57) ABSTRACT

A suction cleaning apparatus or suction cleaning horn is a generally cylindrical barrel or sleeve with an insertion cone to control and direct the distal tip of a suction tool into the bore of the barrel. A stylet is secured within the suction cleaning barrel and aligned on the longitudinal axis of the bore such that insertion of the suction tool into the cleaning barrel inserts the stylet into the channel of the suction tool to mechanically clear any obstructions of the suction tool. The distal end of the suction cleaning horn may also include one or more holes or vents to permit cleaning liquid to be drawn into the bore of the cleaning horn and into the suction tool channel to help clear obstructions in the suction tool.

5 Claims, 4 Drawing Sheets

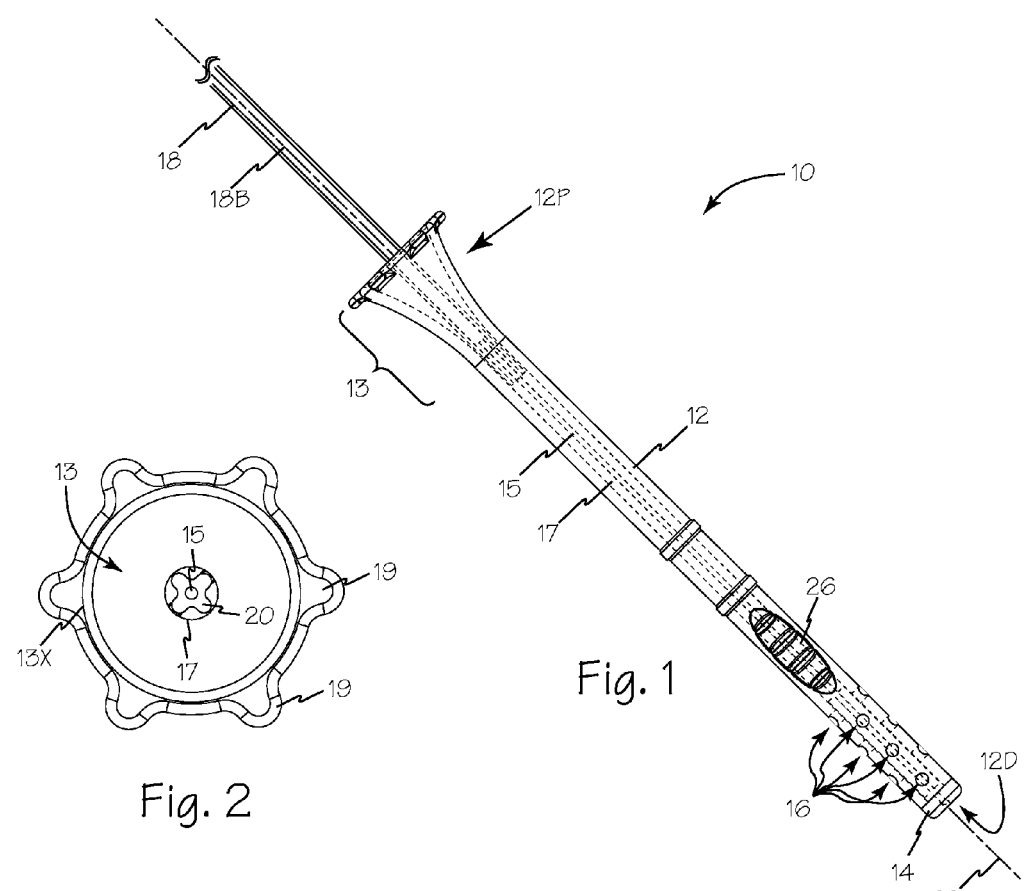
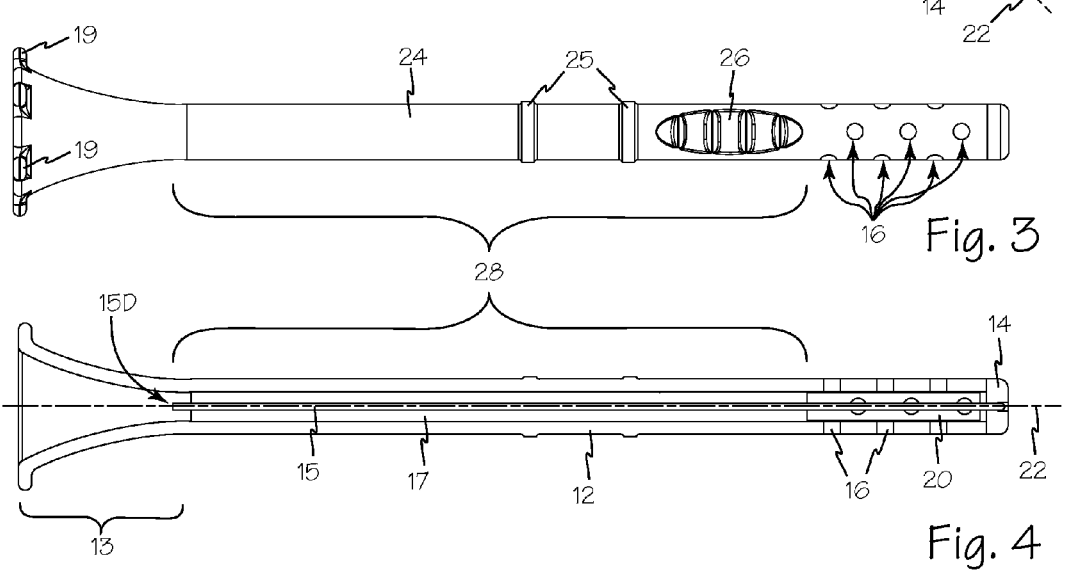

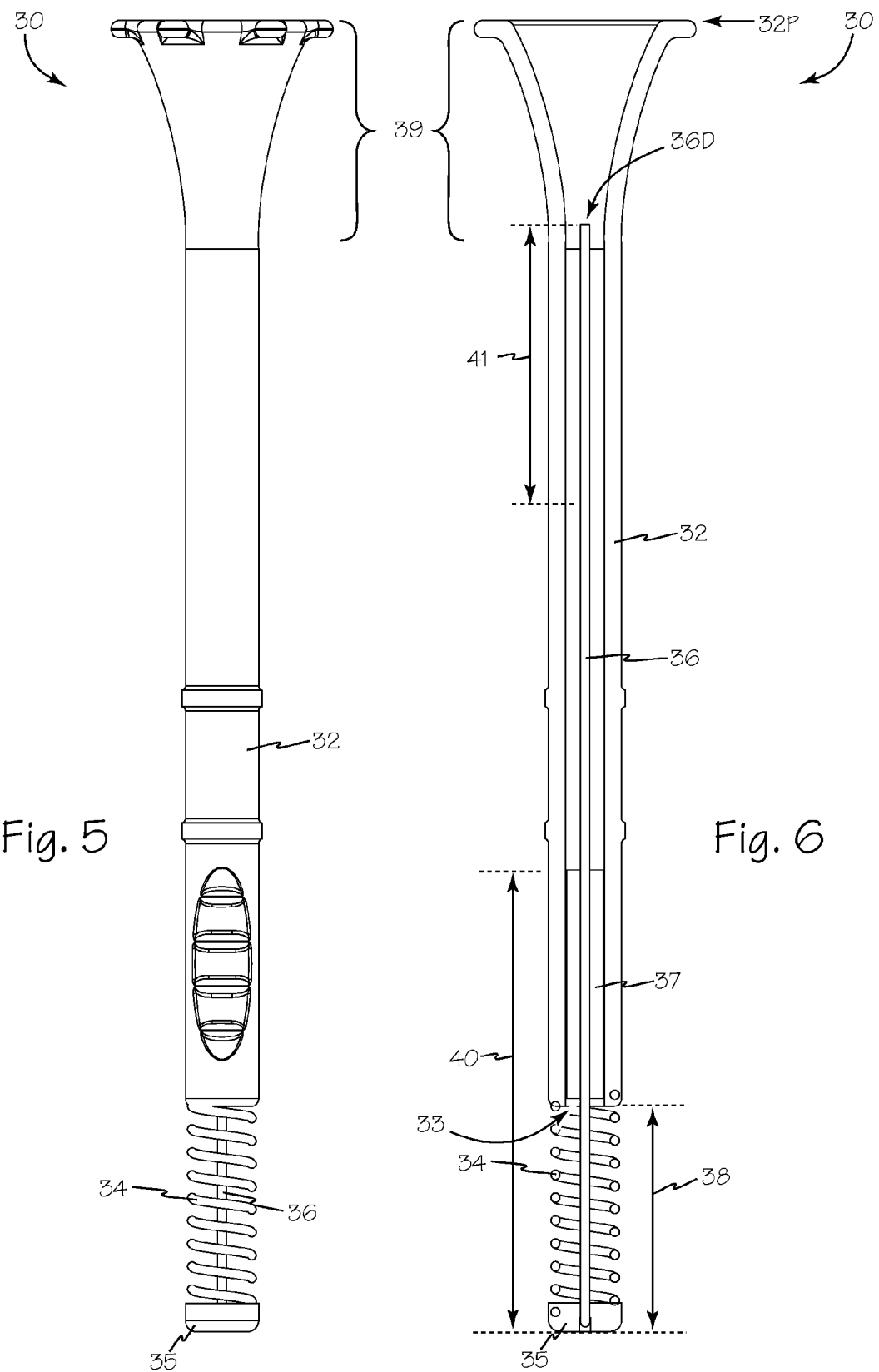

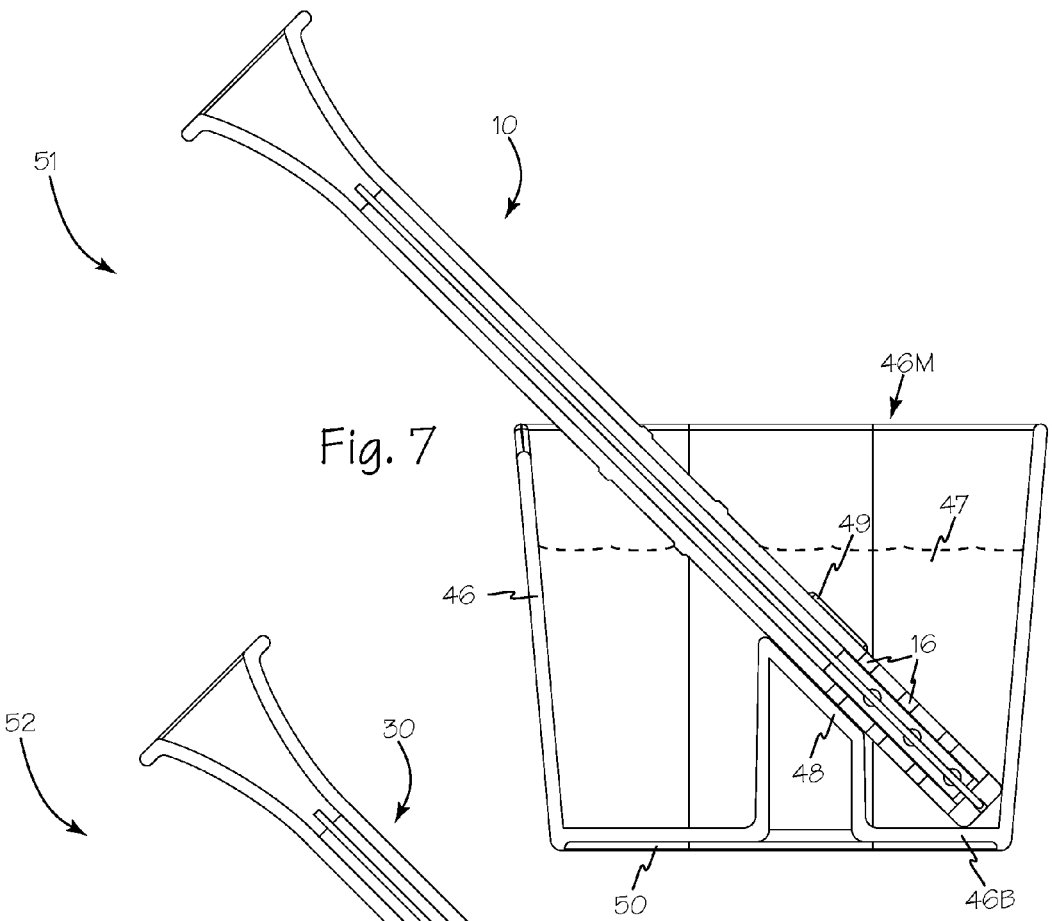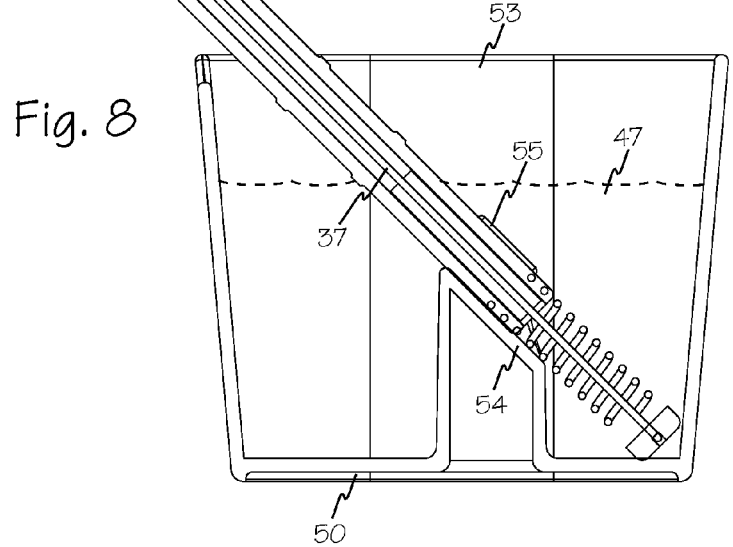

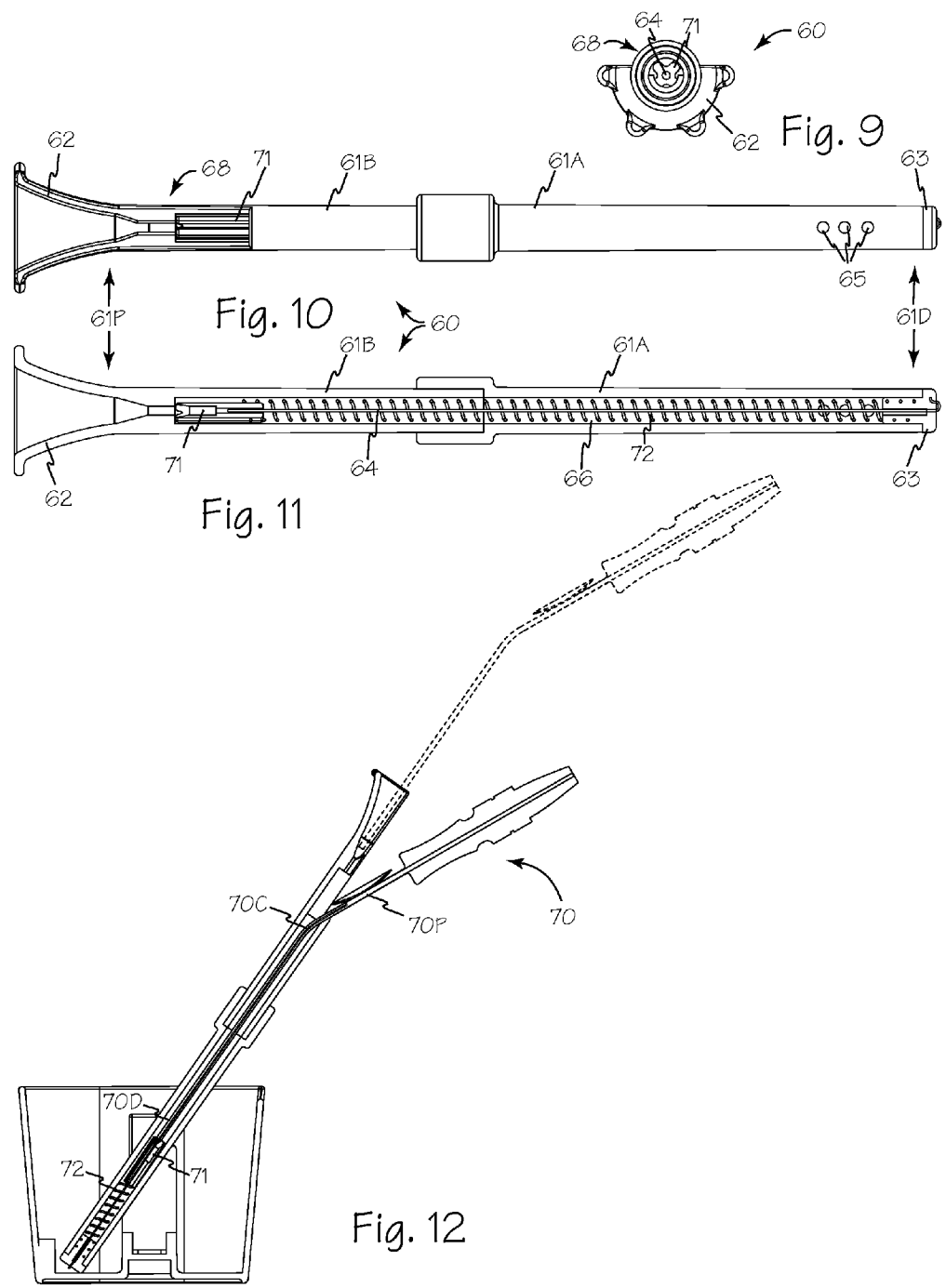

MEDICAL SUCTION CLEARING APPARATUS

RELATED APPLICATIONS

This application claims priority from U.S. Provisional Patent Application 61/423,015 filed Dec. 14, 2010.

FIELD OF THE INVENTIONS

The inventions described below relate to the field of surgical tools and more specifically to surgical tools for clearing obstructions in surgical suction devices.

BACKGROUND OF THE INVENTIONS

Surgical procedures are complicated, dangerous and expensive. The tools used by surgeons are selected to provide the greatest utility and efficiency to achieve optimal outcomes for the patient. A basic tool used in virtually every surgical procedure is suction, which is implemented through a slender tube. During surgery, the suction tube may become clogged with tissue being removed from the surgical site. Once clogged, the suction apparatus requires a surgical assistant to clear the obstruction to enable the surgery to continue. With surgery costs into the hundreds of dollars per minute, every minute wasted is expensive and potentially dangerous for the patient.

SUMMARY

A suction cleaning apparatus or suction cleaning horn as described below is a generally cylindrical barrel or sleeve with an insertion cone to control and direct the distal tip of a suction tool into the bore of the barrel. A stylet or other suitable shaft is secured within the suction cleaning barrel and aligned with the longitudinal axis of the bore such that insertion of the suction tool into the cleaning barrel inserts the stylet into the lumen of the suction tool to mechanically clear any obstructions of the suction tool. The distal end of the suction cleaning horn may also include one or more holes or vents to permit cleaning liquid or air to be drawn into the bore of the cleaning horn and into the lumen of the suction tool to help clear obstructions in the suction tool.

In another configuration of the suction cleaning apparatus as described below, the distal end of the suction cleaning barrel has an extended spring replacing a portion of the barrel and securing the endcap and the stylet. The spring style cleaning apparatus enables the use of a flexible stylet that can be pushed up into a curved suction lumen to clear an obstruction that has become lodged well into the suction lumen. The spring portion of the barrel also enables cleaning solution or air to be drawn through the spring and into the cleaning barrel and thus into the suction lumen to help clear obstructions.

In yet another configuration of the suction cleaning apparatus as described below, the barrel may include an internal spring for urging the spacer toward the insertion cone to keep the stylet covered until a suction tip is inserted into the insertion cone and overcomes the spring force and pushes the spacer distally into the bore of the cleaner barrel and simultaneously pushes the stylet into the suction tip to mechanically dislodge any obstructions therein.

In still another configuration of the suction cleaning apparatus described below, the insertion cone may include a cutout or window to permit a curved tip of a suction tool to be fully inserted into the barrel of the cleaning apparatus without the curve of the suction tip engaging the insertion cone.

A cup or reservoir includes one or more structures to secure and orient a suction cleaning apparatus with the distal end of the barrel and the one or more openings or vents therein below the surface of cleaning fluid contained within the reservoir.

The devices and methods described below provide for a cleaning apparatus to be provided for every procedure requiring suction to enable a surgeon or other operator to quickly clear an obstructed suction tool without surrendering the suction tool.

BRIEF DESCRIPTION OF THE DRAWINGS

FIG. 1 is a side view of a suction cleaning horn with a surgical suction tool inserted.
FIG. 2 is an end view of a suction cleaner apparatus looking into the insertion cone.
FIG. 3 is a side view of a suction cleaning horn.
FIG. 4 is a cross section of the suction cleaning horn of FIG. 3.
FIG. 5 a side view of an alternate suction cleaning horn.
FIG. 6 is a cross section view of the suction cleaning horn of FIG. 5.
FIG. 7 is a cross section of a suction cleaning horn secured in a cleaning cup.
FIG. 8 is a cross section of an alternate suction cleaning horn secured in a cleaning cup.
FIG. 9 is an end view of another alternate suction cleaner apparatus looking into the insertion cone.
FIG. 10 is a side view of another alternate suction cleaning horn.
FIG. 11 is a cross section of the suction cleaning horn of FIG. 10.
FIG. 12 is a cross section of suction cleaning horn of FIG. 10 secured in a cleaning cup.

DETAILED DESCRIPTION OF THE INVENTIONS

Suction cleaning horn or cleaning apparatus 10 is illustrated in FIGS. 1, 2, 3 and 4. Suction cleaning apparatus 10 includes body or barrel 12 with insertion cone 13 formed in proximal end 12P, and in this configuration, distal end 12D is closed by endcap 14. Endcap 14 engages and secures a stylet or any other suitable mechanical cleaning shaft such as shaft 15. There may be one or more vents, ports or holes such as vents 16 in fluid communication with internal bore 17 to permit the flow of cleaning fluid and or air into bore 17 to be drawn into a suction tube such as lumen 18B of suction tube 18.

Referring now to FIG. 2, insertion cone 13 may adopt any suitable shape for controlling, aligning and directing an obstructed suction tube into bore 17. In the side views of FIGS. 1 and 4, insertion cone 13 is a generally round funnel or cone. With the shape of barrel 12 being round and insertion cone 13 also round, extensions, tips or other suitable elements such as fingers 19 may be formed into or added to edge 13X of insertion cone 13 to prevent suction cleaning apparatus 10 from rolling when laid down and to improve a users control of the suction cleaning apparatus in use. Looking down into bore 17, shaft 15 is secured by spacer 20 to be concentric and aligned with longitudinal axis 22 of the cleaning horn.

Referring now to FIG. 3, outside surface 24 of the cleaning horn may also include one or more elements to improve a users control of the cleaning horn when in use. For example, one or more ridges 25 or slots may be raised above or cut into outside surface 24 respectively. Grip areas such as grip area 26 may also be added to improve a users control of cleaning horn 10. Useful length 28 of shaft 15 may be selected to correspond to the length of suction tube 18 for which suction cleaning horn 10 is generally expected to be used. Useful length 28 is measured from the shaft distal end 15D to spacer 20.

Referring now to FIGS. 5 and 6, suction cleaning horn 30 includes the features and elements of suction cleaning apparatus 10. Distal end 32D of barrel 32 includes opening 33 and spring 34 which engages and secures endcap 35 which in turn secures cleaning shaft 36. In this configuration, spacer 37 loosely secures shaft 36 to permit shaft 36 to slide through the spacer when spring 34 is compressed to push shaft 36 into a clogged suction lumen. Uncompressed length 38 of spring 34 may be selected to enable shaft 36 to extend well beyond proximal end 32P of the cleaning horn when spring 34 is fully compressed. Shaft 36 may also be selected to have some flexibility to enable it to clear curved suction tubes. The combination of a long spring and a flexible shaft enables a curved suction tube to easily engage the distal end 36D of cleaning shaft 36 in insertion cone 39, and subsequent compression of spring 34 will cause flexible shaft 36 to extend through and beyond insertion cone 39 and well into the curved suction lumen to clear any obstructions in the suction lumen. Shaft 36 may have different characteristics in different portions of the shaft, such as for example, proximal portion 40 may be stiff and smooth to enable smooth compression of the spring and secure retention of shaft 36 in endcap 35. Distal portion 41 may be flexible as discussed and may also have a rough finish to provide improved mechanical cleaning for a clogged suction lumen.

Referring now to FIG. 7, cleaning system 51 includes a cleaning cup such as cleaner cup 46 configured with a suitable securing means such as a clip, latch or frictional opening to secure a suction cleaning horn such as cleaning horn 10 in a suitable orientation with barrel 12 and insertion cone 13 extending out through cup mouth 46M and barrel 12 extending into the cup to maintain one or more opening such as vents 16 below the surface of cleaning fluid 47 and near cup bottom 46B. A support such as support 48 may also include a securing or engagement means such as clip 49 to further engage cleaning horn 10. With cleaning horn 10 secured to cup 46 or support 48 in a suitable quantity of cleaning fluid 47, a user with a clogged suction tube may simply push the clogged suction tube into insertion cone 13 without the need for the user's other hand to hold the cleaning horn. Cleaning cup 46 may also include a friction layer or adhesive layer such as adhesive layer 50 to facilitate single-handed use of cleaning system 51.

Referring now to FIG. 8, cleaning system 52 includes a cleaning cup such as cleaner cup 53 configured with a suitable securing means to secure a suction cleaning horn such as cleaning horn 30 in a suitable orientation to maintain spring 34 below the surface of cleaning fluid 47. Support 54 may also include a securing or engagement means such as clip 55 to frictionally engage cleaning horn 30. With cleaning horn 30 secured to a securing means such as clip 55 or support 54 in a suitable quantity of cleaning fluid 47, a user with a clogged suction tube may simply push the clogged suction tube into insertion cone 39 without the need for the user's other hand to hold the cleaning horn. When the distal end of the clogged suction tube contacts spacer 37, any additional pressure by the user causes cleaning horn to slide between clip 55 and support 54 which compresses spring 34 and forces shaft 36 into the clogged suction lumen. Release of pressure by the user allows spring 34 to extend and restores cleaning system 52 to the ready position.

Referring now to FIGS. 9, 10 and 11, alternate cleaning horn 60 includes a separable body or barrel composed of end portion 61A and cone portion 61B with insertion cone 62 formed in proximal end 61P, and in this configuration, distal end 61D is closed by endcap 63. Endcap 63 engages and secures a stylet or any other suitable mechanical cleaning shaft such as shaft 64. There may be one or more vents, ports or holes such as vents 65 in fluid communication with internal bore 66 to permit the flow of cleaning fluid and or air into bore 66. Alternate cleaning horn has opening or window 68 in the control cone 62. Window 68 enable a curved suction tube such as suction tube 70 to be inserted into bore 66 deep enough to enable stylet 64 to extend through curve 70C into proximal end 70P as shown in FIG. 12. Spacer 71 moves freely within bore 66 and is urged into proximity of insertion cone 62 by spring 72.

As illustrated in FIG. 12, insertion of distal tip 70D of suction tube 70 into insertion cone 62 enables the distal tip to push spacer 71 distally through barrel 61 and compress spring 72 into distal end 61D. Distal movement of spacer 71 exposes stylet 64 and enables the stylet to enter the distal tip of the suction tube to be cleared. A flexible stylet such as stylet 64 may follow curve or curves of a suction tube such as curve 70C as the stylet moves up into the suction tube.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A suction cleaning apparatus comprising:
 a generally cylindrical barrel having a hollow bore and a first end and a second end, the barrel having a longitudinal axis extending collinear with the hollow bore;
 an endcap engaging and closing the second end of the barrel;
 one or more vents near the second end of the barrel, the one or more vents extending through the barrel in fluid communication with the hollow bore;
 a stylet secured in the endcap and extending along the longitudinal axis within the bore; and
 an insertion cone formed in the first end of the barrel to control and direct a suction apparatus into the bore.

2. The suction cleaning apparatus of claim 1 further comprising a spacer within the bore, the spacer frictionally engaging the bore of the barrel near the second end of the barrel, the spacer also frictionally engaging the stylet.

3. The suction cleaning apparatus of claim 1 further comprising:
 a cleaning cup having an open mouth, a closed bottom and a retaining means sized to engage the barrel with the second end of the barrel near the bottom of the cleaning cup.

4. The suction cleaning apparatus of claim 1 further comprising:
 a spring having a first and second end, the first end of the spring engaging and extending from the second end of the barrel, the spring coiled around the longitudinal axis of the barrel, the endcap engaging the second end of the spring with the stylet extending through the spring and the barrel.

5. A suction cleaning system comprising:
- a generally cylindrical barrel having a hollow bore and a first end and a second end, the barrel having a longitudinal axis extending collinear with the hollow bore and one or more vents near the second end, the vents extending through the barrel in fluid communication with the hollow bore;
- a spring having a first and second end, the first end of the spring secured to, and extending from the second end of the barrel, the spring coiled around the longitudinal axis of the barrel
- an endcap secured to the second end of the spring;
- a stylet secured in the endcap and extending along the longitudinal axis within the spring and the bore;
- a spacer within the bore, the spacer frictionally engaging the bore of the barrel near the second end of the barrel, the spacer also frictionally engaging the stylet;
- an insertion cone formed in the first end of the barrel to control and direct a suction apparatus into the bore; and
- a cleaning cup having an open mouth, a closed bottom and a retaining means sized to engage the barrel with the second end of the barrel near the bottom of the cleaning cup.

* * * * *